(12) United States Patent
Rezanezhad Gatabi

(10) Patent No.: US 10,607,772 B2
(45) Date of Patent: Mar. 31, 2020

(54) CONDUCTIVITY AND IMPEDANCE SENSOR

(71) Applicant: R-Water LLC, San Marcos, TX (US)

(72) Inventor: Javad Rezanezhad Gatabi, San Marcos, TX (US)

(73) Assignee: R-Water LLC, San Marcos, TX (US)

( * ) Notice: Subject to any disclaimer, the term of this patent is extended or adjusted under 35 U.S.C. 154(b) by 0 days.

(21) Appl. No.: 14/721,444

(22) Filed: May 26, 2015

(65) Prior Publication Data

US 2015/0348701 A1    Dec. 3, 2015

Related U.S. Application Data

(60) Provisional application No. 62/004,618, filed on May 29, 2014, provisional application No. 62/037,187, filed on Aug. 14, 2014.

(51) Int. Cl.
| | | |
|---|---|---|
| *G01F 23/24* | (2006.01) | |
| *H01F 27/40* | (2006.01) | |
| *G01F 23/22* | (2006.01) | |
| *G01N 27/02* | (2006.01) | |
| *G01R 27/02* | (2006.01) | |
| *H01F 27/24* | (2006.01) | |
| *H01F 27/28* | (2006.01) | |

(52) U.S. Cl.
CPC .......... *H01F 27/402* (2013.01); *G01F 23/22* (2013.01); *G01F 23/24* (2013.01); *G01N 27/023* (2013.01); *G01R 27/02* (2013.01); *H01F 27/24* (2013.01); *H01F 27/2823* (2013.01)

(58) Field of Classification Search
CPC .. G01N 27/02–10; G01N 27/22; G01R 27/22; G01F 23/24–241

USPC ........ 324/439–450, 228–243, 204, 693–701, 324/691

See application file for complete search history.

(56) References Cited

U.S. PATENT DOCUMENTS

| | | | | |
|---|---|---|---|---|
| 3,015,061 A | * | 12/1961 | Boeke | G01N 27/025 324/204 |
| 3,417,329 A | * | 12/1968 | Landis | G01N 27/025 324/445 |
| 3,447,073 A | * | 5/1969 | Gamble | G01N 27/74 324/204 |
| 3,603,873 A | * | 9/1971 | Cirulis | G01N 27/023 324/445 |
| 3,806,798 A | * | 4/1974 | Gross | G01R 27/22 324/445 |
| 3,855,522 A | * | 12/1974 | Kobayashi | G01N 27/023 324/445 |
| 3,987,362 A | * | 10/1976 | McCann | G01F 1/582 324/445 |

(Continued)

FOREIGN PATENT DOCUMENTS

GB    1235646 A    6/1971

*Primary Examiner* — Patrick Assouad
*Assistant Examiner* — Demetrius R Pretlow
(74) *Attorney, Agent, or Firm* — David S Nagy

(57) ABSTRACT

A conductivity sensor, preferably a structure with a pair of magnetic cores with a primary coil wire around a shared member of both cores, and a secondary coil wire around a non-shared section of each core. When part of one core is immersed in a fluid and current is applied to the primary coil, measurements taken at the secondary coils reveal the conductivity of the fluid. The same structure can be used to measure the level of the fluid, and to determine impedance.

14 Claims, 10 Drawing Sheets

(56) References Cited

U.S. PATENT DOCUMENTS

| | | | | |
|---|---|---|---|---|
| 5,268,642 | A | * 12/1993 | Uchidomi | G01R 27/22 250/551 |
| 5,341,102 | A | * 8/1994 | Akiyama | G01R 27/22 324/202 |
| 2007/0222453 | A1 | * 9/2007 | Reiderman | G01V 3/28 324/333 |
| 2011/0248812 | A1 | 10/2011 | Hu et al. | |
| 2013/0021042 | A1 | * 1/2013 | Lammel | G01R 27/22 324/654 |
| 2015/0226683 | A1 | * 8/2015 | Feldman | A01J 5/0133 324/640 |
| 2015/0273126 | A1 | * 10/2015 | Beiriger | A61M 1/1601 210/647 |

* cited by examiner

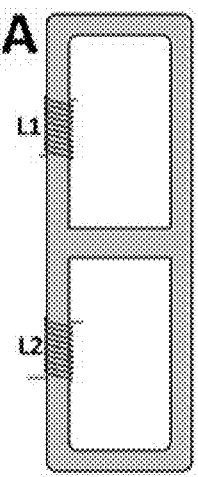 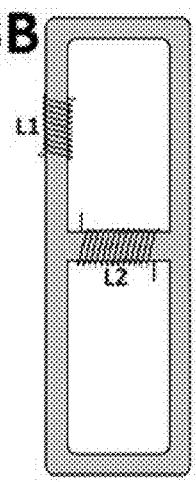 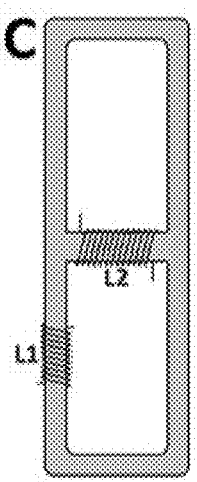
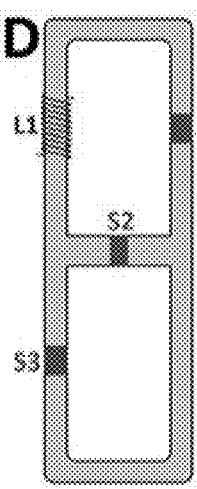 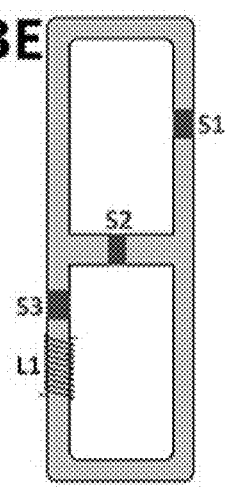 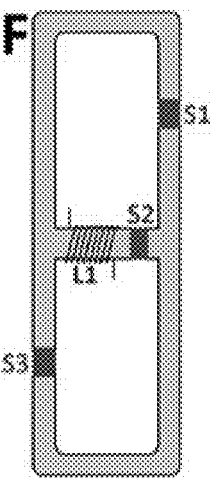
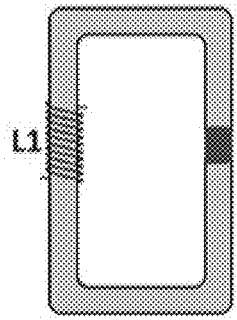 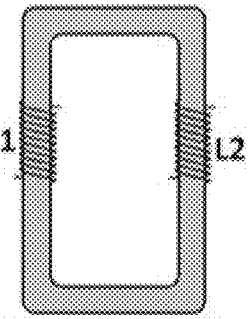 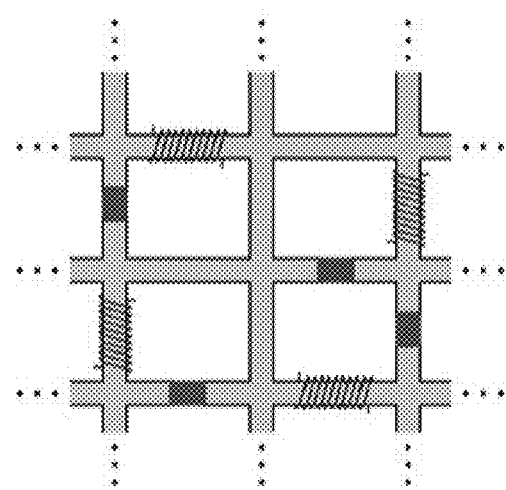

CONDUCTIVITY AND IMPEDANCE SENSOR

BACKGROUND OF THE INVENTION

Sensors that detect and measure the conductivity of fluids are useful for a variety of purposes. U.S. patent application Ser. No. 11/402,0062 by Guest, for example, offers a novel method and apparatus for controlling electrolytic processes purely through such conductivity measurements, rather than by the more traditional measurement of the pH or oxidation reduction potential of the electrolyzed product. While that invention offers a simpler and more reliable way to control such processes, a simpler—and thus implicitly more reliable—conductivity sensor would improve that innovation further, and be of great benefit in a variety of other applications, as well. Current sensors require complex circuitry and measurements, and are subject to degradation by the accumulation of deposits on sensor surfaces; also, when used to measure the conductivity of materials with low conductivity—such as water—they can see very low voltages at the receiver coil, resulting in inaccurate measurements overwhelmed by background "noise" from stray electromagnetic waves in the environment and similar. This invention has none of these drawbacks.

BRIEF SUMMARY OF THE INVENTION

In its simplest form, this invention consists of two rectangular magnetic cores joined together, like a digital readout rendering of the number eight. This figure eight is provided with a primary wire coil wrapped around the common member of the two cores, i.e., the central cross-bar of the eight, as well as two secondary wire coils, one to each core, wrapped around a section of the figure eight other than the common member. One core is at least partially immersed in or surrounded by the material whose conductivity is to be measured—the target material—and a voltage is applied to the primary coil—in practice, AC is generally preferred, but DC can also be advantageously used for certain applications, for example with target materials exhibiting high resistance. Measurement is achieved by one of three methods: either by measuring the signal of a secondary coil with the aid of an amplifier and analog circuits or by digital sampling and software calculation; by measuring the differential signal of the secondary coils with the aid of a differential amplifier or by digital sampling and software calculation; or else by connecting the secondary coils in series, and measuring the signal at the two ends of those series-connected coils.

BRIEF DESCRIPTION OF THE SEVERAL VIEWS OF THE DRAWINGS

FIGS. 3A, 3B, 3C, 3D, 3E, 3F, 3G, 3H and 3I show a variety of embodiments, including different coil arrangements, the employment of magnetic sensors, single-core embodiments and a matrix employing more than two cores.

DETAILED DESCRIPTION OF THE INVENTION

In its basic form, this invention comprises two magnetic cores joined together. While this shape is most easily conceived and described as a pair of rectangles joined to form a rectangular figure eight (FIGS. 1A, 1C and 1D), is can readily be understood that these cores can effectively be made in a wide variety of shapes, and that they need not be identical to each other (FIG. 1B); the only requirement is that each of the cores describe a closed path.

Figure 1A:
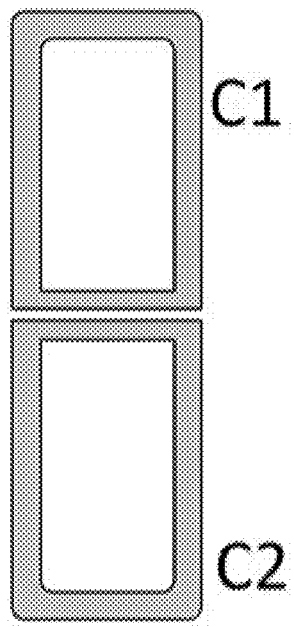
FIGS. 1A, 1B, 1C and 1D show four views of the dual cores, as a single unit, as two unitary cores joined together, with the cores consisting of multiple pieces joined together, and as other than rectangles.
Figure 1B:
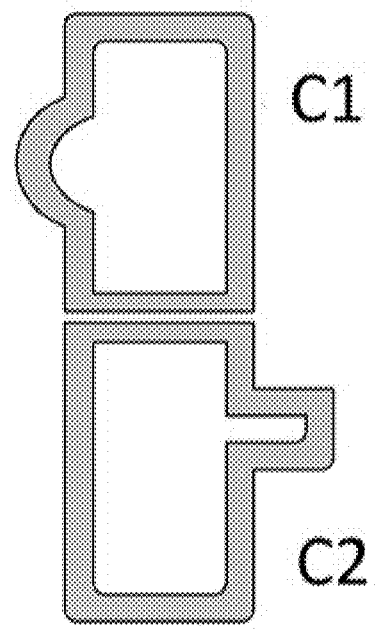
Figure 1C:
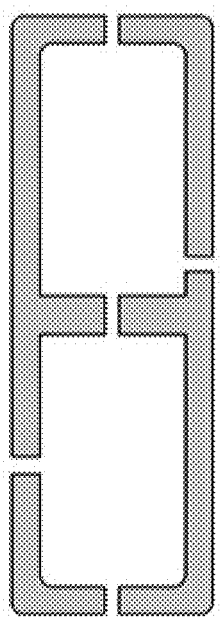
Figure 1D:
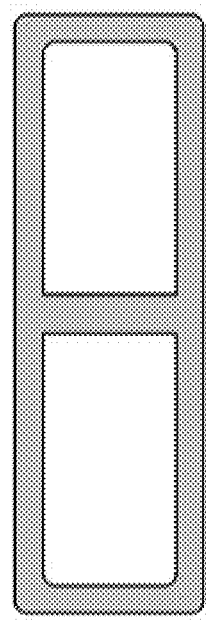

Similarly, while FIG. 1A shows two unitary cores closely mated, it is possible to have these individual cores be composed of several parts (FIG. 1C).

In practice, barring unusual application requirements that would mandate the use of sensor cores in unusual shapes or comprised of multiple parts, it is particularly easy to produce, to use and, most certainly, to describe a one-piece rectangular figure eight sensor (FIG. 1D), though it can be readily understood how these descriptions apply to other variants, as well.

Figure 2A:
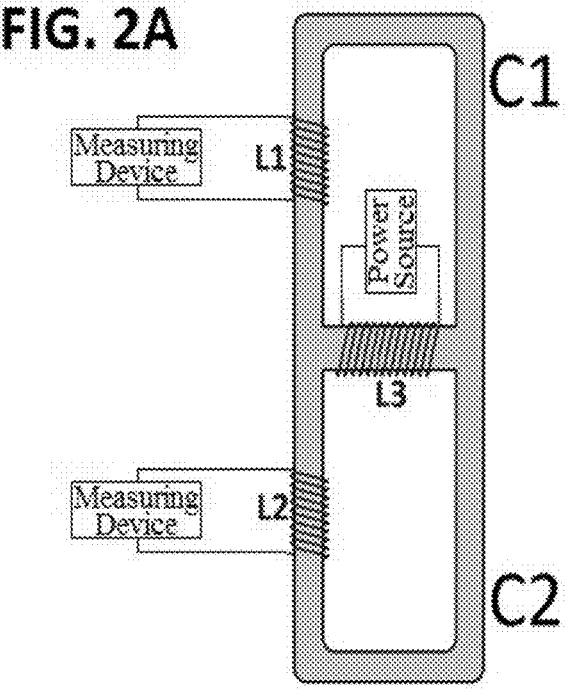
FIGS. 2A and 2B show a unitary dual core embodiment with coils wired in two variations.
Figure 2B:
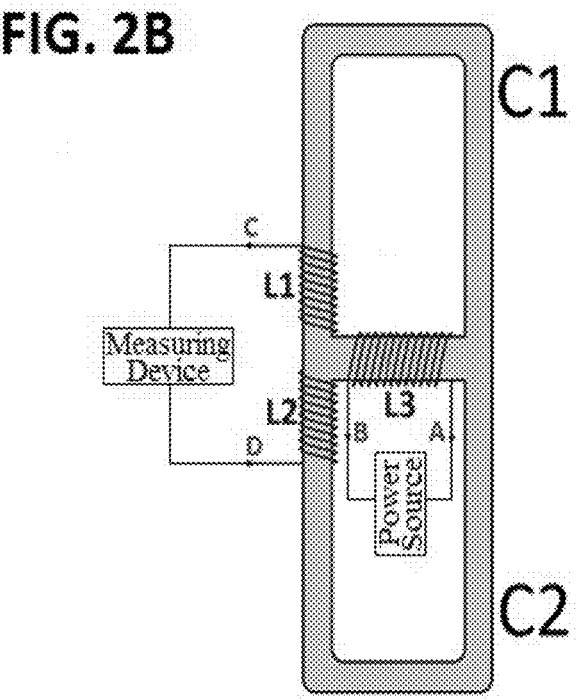
Figure 4:
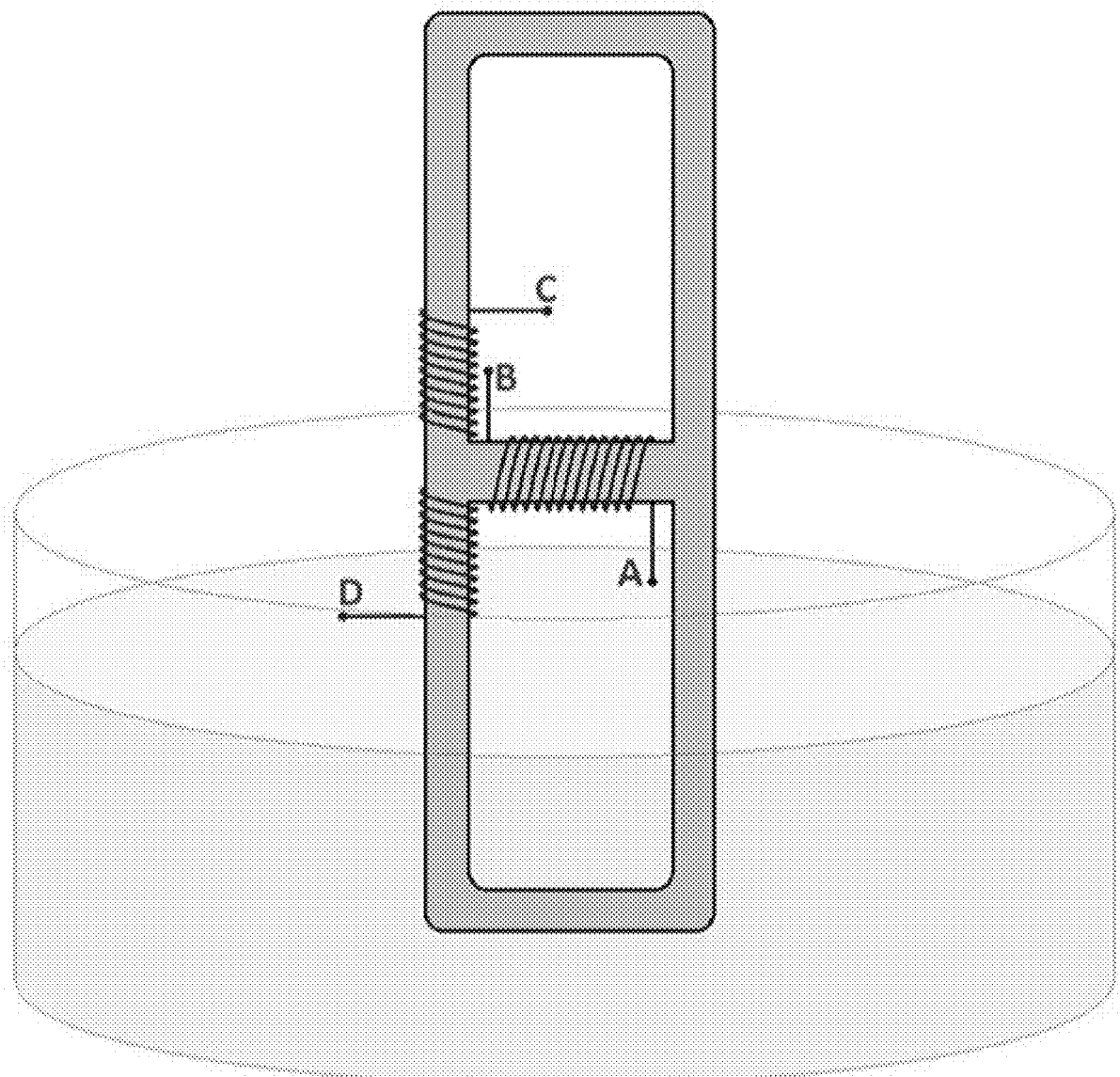
FIG. 4 shows a sensor according to FIG. 2B with one of its cores partially surrounded by a target material, and the other core not surrounded by such material.
Figure 5:
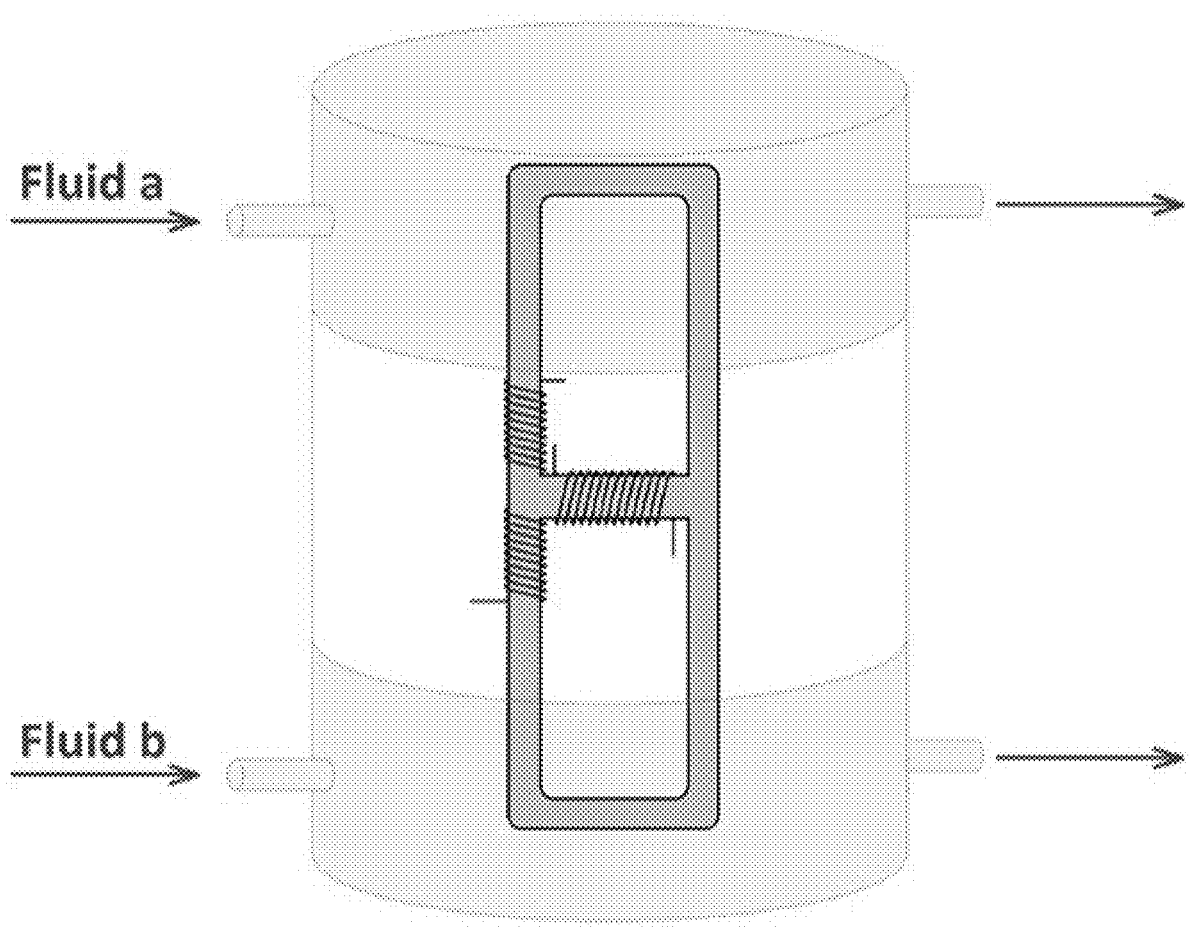
FIG. 5 shows a sensor according to FIG. 2B with one of its cores partially surrounded by a target material, and the other core partially surrounded by another target material; in this illustration both target materials are fluids.

FIGS. 2A and 2B show the basic wiring arrangement. A joint or common electrical coil L3 is wound around the common member, the cross-bar of the figure eight—what would be the area where, in a separate-core embodiment, the cores mate up. Furthermore, a first individual coil L1 is wound around some portion of first core C1 other than the common member, and a second individual coil L2 is wound around some portion of second core C2 other than the common member.

This wiring arrangement can be maintained as three separate coils, as in FIG. 2A, in which case the sensor operates by immersing one of the cores in the target material, optionally immersing the other core in a second target material, applying an electrical signal to common coil L3, and measuring the differential signal reading at individual coils L1 and L2 using an electronic circuit employing a differential amplifier or—and the irony in this phrasing is understood—its digital analog, digital sampling coupled with a software calculation.

In a preferred embodiment shown in FIG. 2B, individual coils L1 and L2 are connected in series. In this embodiment the sensor operates by immersing one of the cores in the target material, optionally immersing the other core in a second target material, applying an electrical signal to common coil L3, and measuring the signal at points C and D, the terminations of the joined individual coils L1 and L2.

The scheme described in the two preceding paragraphs can also be reversed electrically: in the preferred embodiment by applying the electrical signal to points C and D on joined individual coils L1 and L2, and by measuring the signal at points A and B on common coil L3, or in the earlier-mentioned embodiment by applying two signals which need not be identical, one each to individual coils L1 and L2, and measuring the signal at common coil L3. The preferred embodiment is as described in the prior paragraph, and further descriptions will be of that embodiment, though it can be readily understood how they can be applied to the other embodiments mentioned.

The signal measurement taken may be simple voltage or current amplitude, or voltage or current phase, or any combination of these, as all will yield useful information about the conductivity of the target material. The measurements may be done in either time-domain or frequency-domain, using Discrete Fourier Transform (DFT) or Fast Fourier Transform (FFT).

Figure 6:
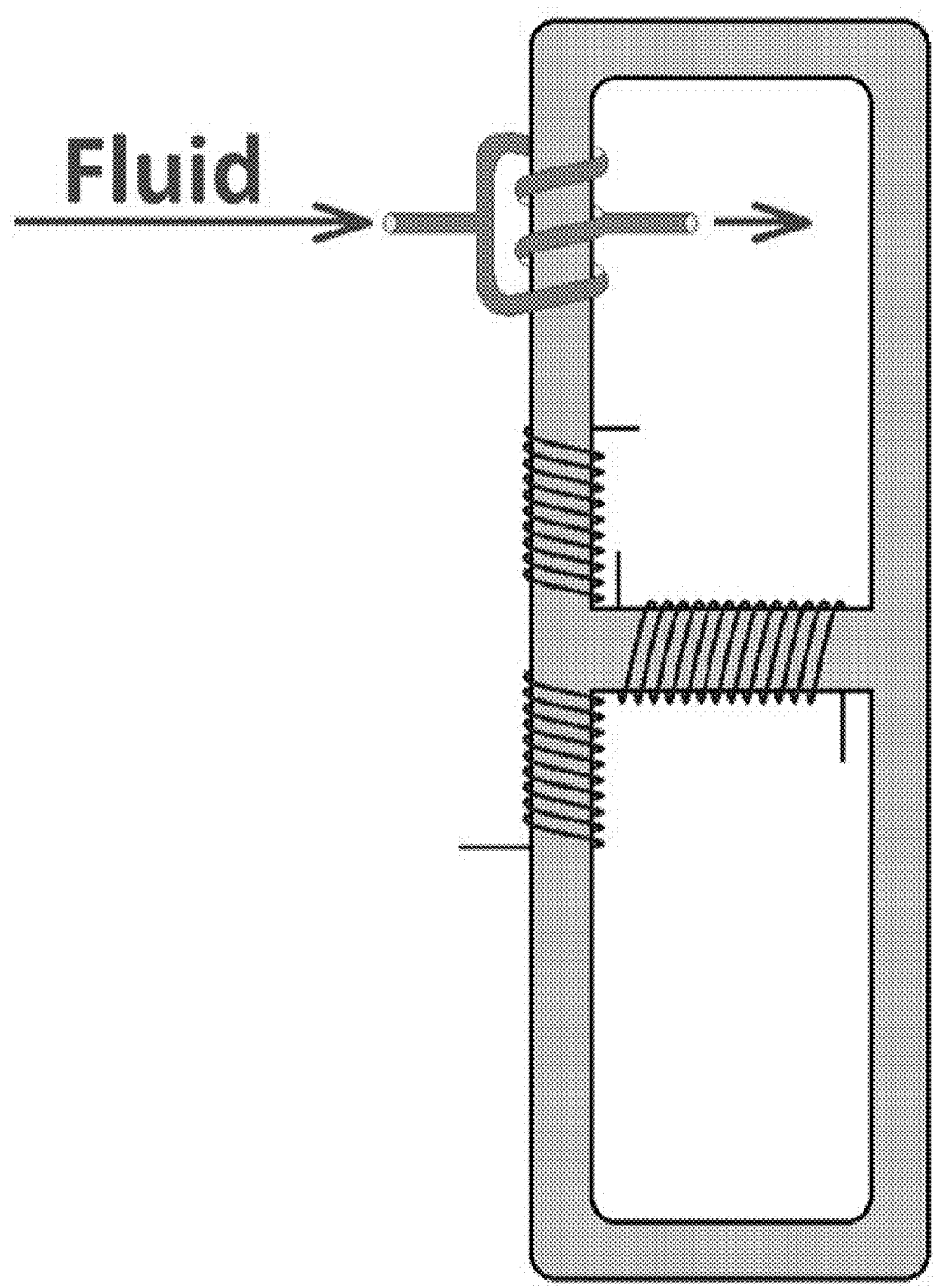
FIG. 6 shows an embodiment in which target material fluid is ducted around a wall of a core.

While the most common application of this sensor will be for measuring the conductivity of fluids by immersing a core in a fluid, it is also possible to cast or build solid material around the sensor. It is also possible to use the sensor by having fluid target material ducted through a hose or pipe or similar conduit that passes through the magnetic path of one of the cores, e.g., a hose coiled around one of the sides of C1 other than the common member, as shown in FIG. 6. In much the same way, a solid target material could be placed in the magnetic path of one of the cores, e.g., a plastic rod encircling one of the sides of C1 other than the common member.

It must be noted that this invention can also be practiced with conventional magnetic sensors (S1, S2, S3, etc.) in place of, or in addition to, the secondary coil(s) as signal receivers, as shown in FIGS. 3D, 3E and 3F. In such an application, the magnetic sensor(s) would be placed in holes or gaps in the cores and, of course, the transmitting coil—the coil to which the electrical signal is applied—need not be located on the common member, as in FIG. 3F, but can instead be located on one of the non-common sides of a core, as shown in FIGS. 3D and 3E.

Furthermore, the invention can be practiced with both fewer and more than two magnetic cores, as shown in FIGS. 3G/3H, and FIG. 3I, respectively. Again, it is possible to employ magnetic sensors instead of, or in conjunction with, receiving coils. While both single and more-than-two core embodiments are practicable, accuracy and sensitivity tend to suffer in the single-coil embodiment, and do not improve enough in the more-than-two core embodiment to make it generally attractive, so that the "sweet spot" and preferred embodiment for this invention is the dual-core iteration.

Figure 10A:
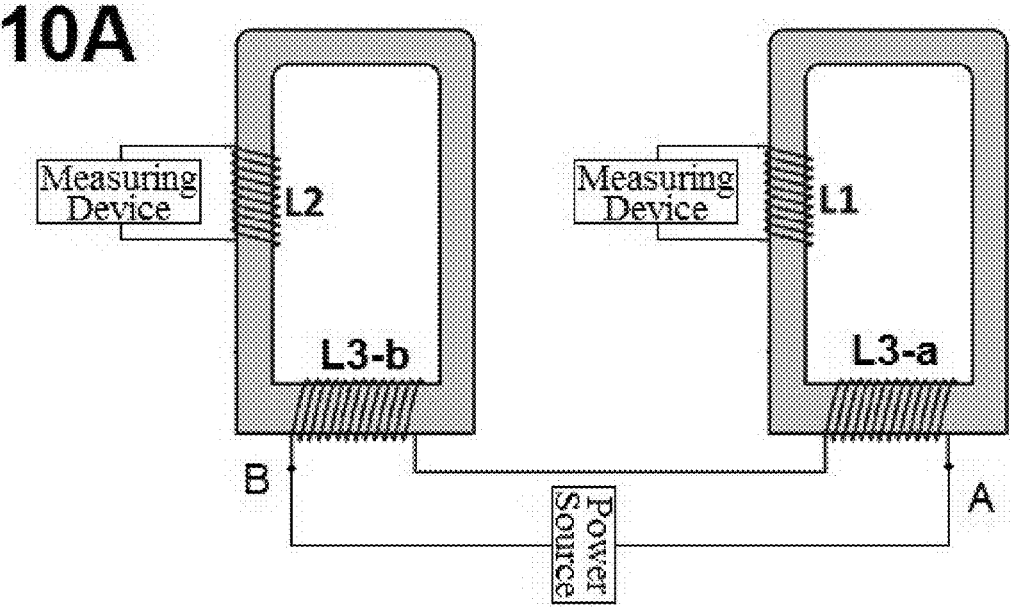
FIGS. 10A and 10B show embodiments of the invention with the cores physically separated with no common member, connected only electrically.
Figure 10B:
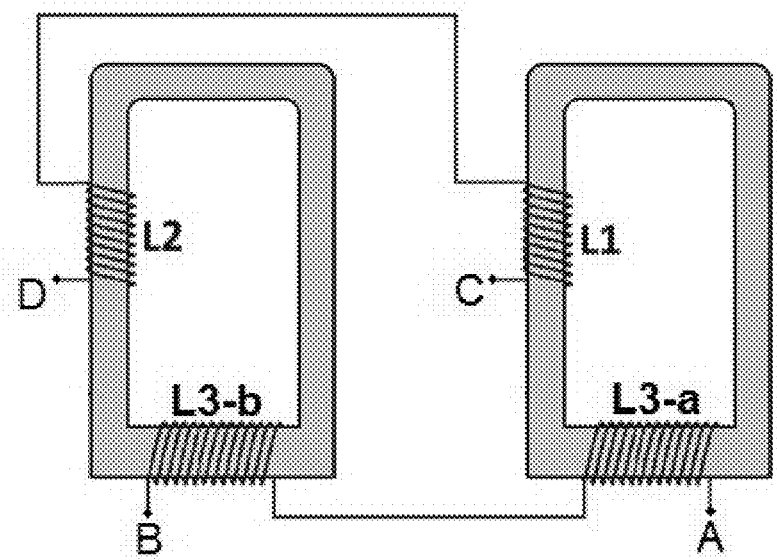

While it is generally helpful, effective and efficient for the cores to share a common member, it is not absolutely necessary. FIGS. 10A and 10B show embodiments with cores that are completely separate physically, connected only electrically. The wiring arrangement in FIG. 10A is analogous to that in FIG. 2A, and that in FIG. 10B is analogous to that in FIG. 2B; as mentioned above, however, instead of series connection of L3-*a* and L3-*b* one may use an analog or digital circuit to control the magnetic flux of L3-*a* and L3-*b*.

The presence of a target material in the magnetic path of one or both cores C1 and C2 affects the signal reading as compared with the reading absent the target material. It can also be helpful to balance any differences in the baseline characteristics of the two cores by equipping one or both cores with at least one additional coil connected to a variable resistor, which can then be adjusted to equalize the magnetic flux of C1 and C2, per FIG. 7.

Figure 8:
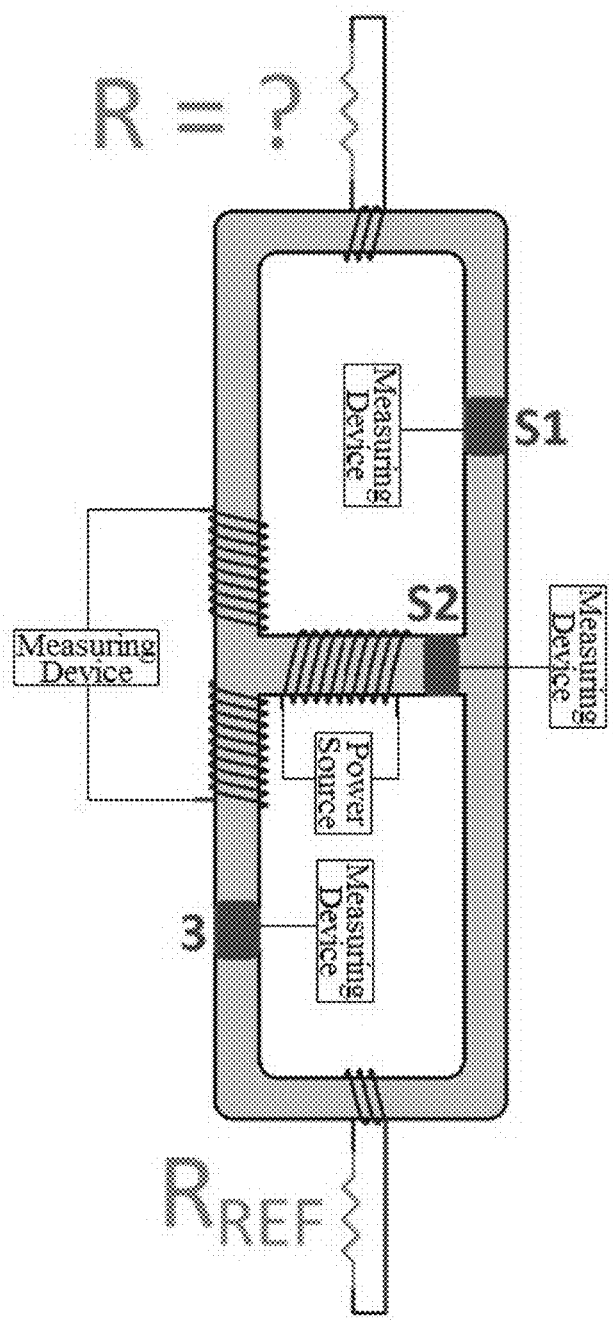
FIG. 8 shows an embodiment of this invention to measure resistance in an unknown circuit with the employment of a reference resistance.

A further application of this invention is for measuring resistance, as shown in FIG. 8. In this embodiment, a reference resistor would be connected to a coil on one core. The target material would be connected to another coil on the other core, and its resistance would affect the readings at receiver coils and/or magnetic sensors, permitting the resistance of the target material to be calculated. A similar structure can be used to measure the differential resistance of two unknown resistors.

Figure 7:
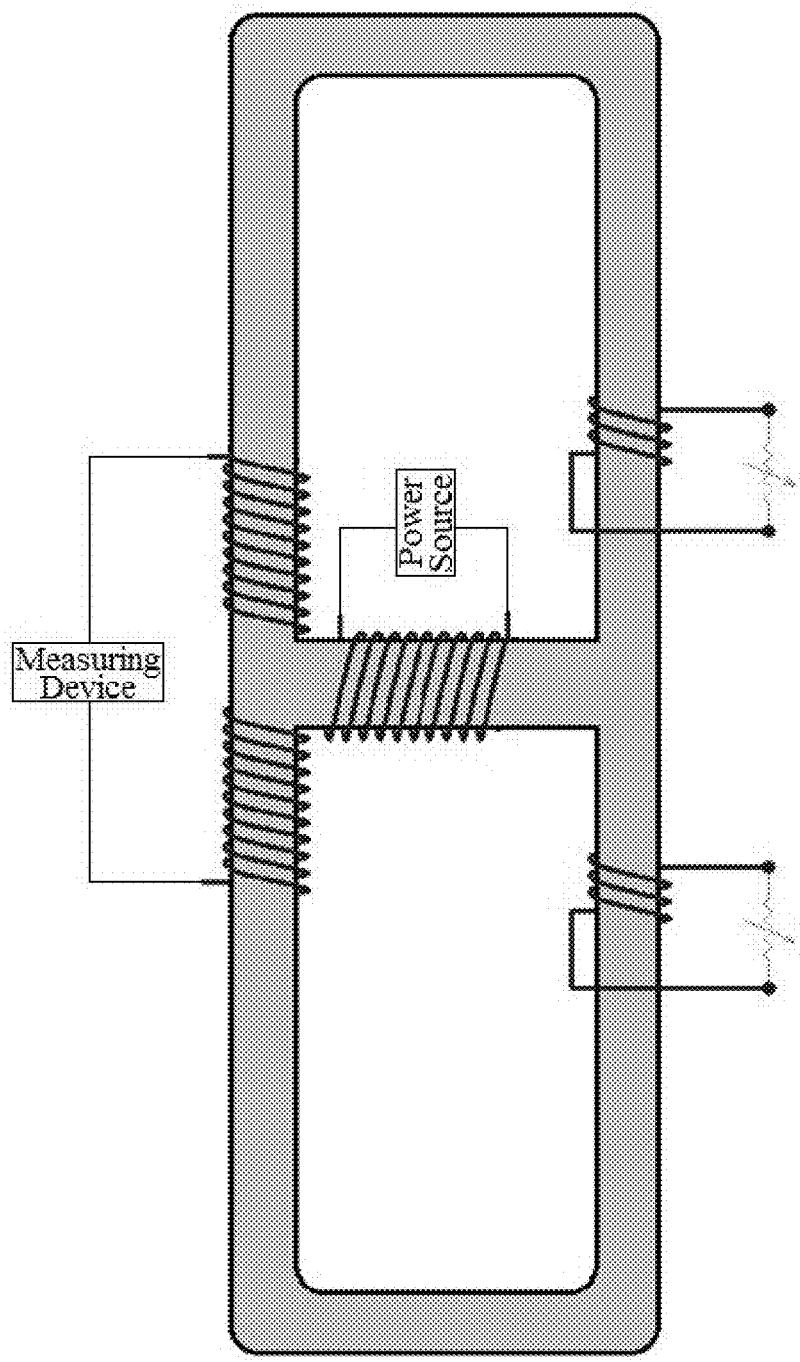
FIG. 7 shows the embodiment of FIG. 2B with an additional coil on each core, each such additional coil connected to a potentiometer for the purpose of balancing the magnetic flux of the two cores.
Figure 9:
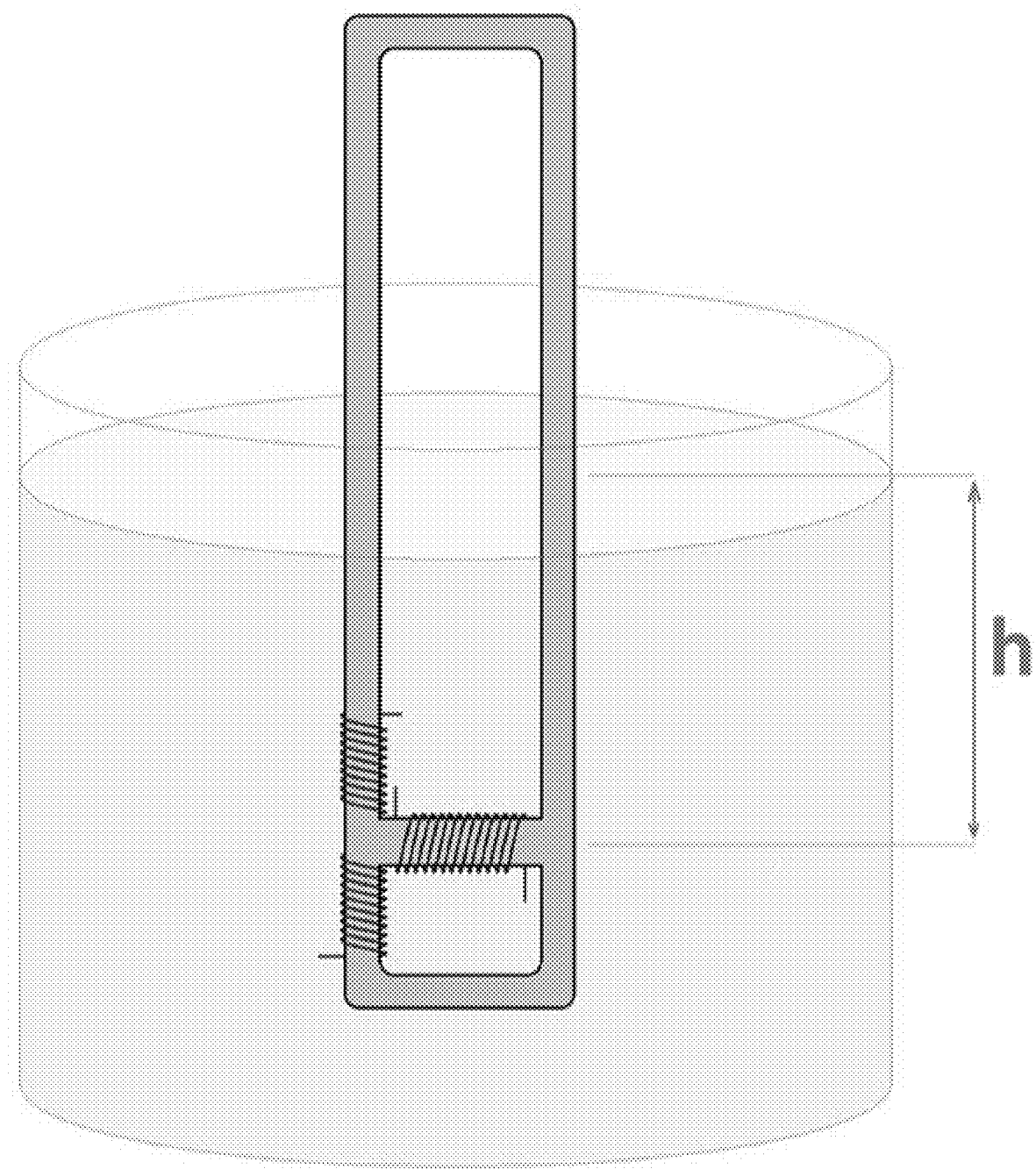
FIG. 9 shows the employment of this invention to measure the level of a fluid.

This invention can also be used to measure the level of a fluid in a container, as shown in FIG. 9. In this application, the core structure would be partially submerged in the target material fluid as shown, with the lower core completely submerged in the fluid, and at least part of the upper core not submerged. As the conductivity readings of the fluid would change as its level drops—or rises—the level can then easily be calculated. To obtain a greater range of level measurement and be able to measure the level closer to empty, it is advantageous to have the cores be asymmetrical, with the upper core taller than the lower core, as shown in FIG. 9. This asymmetricality can distort readings, which distortion can be compensated for in a number of ways, for example by equalizing the magnetic flux of the cores as shown in FIG. 7, by making the walls of the lower core correspondingly thinner, or by applying an equalizing algorithm to the readings.

I claim:

1. A sensor for measuring conductivity or impedance in a test substance, with said sensor at least partially immersed in or surrounded by such test substance, comprising:
    at least one magnetic core, each core comprised of one or more pieces of a magnetic material, with each magnetic core describing a component of a circuit;
    a primary coil wire wrapped around a section of the at least one magnetic core and connected to an electrical power source;
    at least one secondary coil wire wrapped around a section of the at least one magnetic core or at least one magnetic sensor affixed to the magnetic core or both, and:
        electrical connection between a secondary coil or magnetic sensor and a measuring device, which measuring device measures an electrical signal present in such secondary coil or magnetic sensor with the aid of an amplifier and analog circuits, or by digital sampling and software calculation, which measuring may be done in either time-domain, or frequency-domain, using discrete Fourier transform or fast Fourier transform;
        or, in embodiments with a plurality of magnetic cores, and a plurality of secondary coils or magnetic sensors or both, electrical connection between such secondary coils or magnetic sensors or both and:
            a device which measures the differential signal of the secondary coils with the aid of a differential amplifier or by digital sampling and software calculation, which measuring may be done in either time-domain, or frequency-domain, using discrete Fourier transform or fast Fourier transform;
    wherein all such measurements derive from the energy absorption of the test substance.

2. The sensor of claim 1, comprising two magnetic cores in a single piece of magnetic material roughly describing a FIG. 8.

3. The sensor of claim 2, wherein each magnetic core has an additional coil wire wrapped around a section of it and connected to a potentiometer, facilitating the balancing of the flux of the two magnetic cores.

4. The sensor of claim 1, comprising two magnetic cores wholly separate from each other, wherein the primary coil is wrapped around a section of each magnetic core.

5. A sensor for measuring resistance, comprising:
two magnetic cores in a single piece of magnetic material with each magnetic core describing a component of a circuit and the two magnetic cores roughly describing a FIG. 8, so that the two magnetic cores share a common section;
a primary coil wire wrapped around the common section and connected to an AC electrical power source;
a secondary coil wire wrapped around a section of each magnetic core;
another coil wire wrapped around a section of one magnetic core and connected to a first impedance, and yet another coil wire wrapped around a section of the other magnetic core and connected to a second impedance; and
electrical connection between the ends of the secondary coils and a device which measures the signal present in them, including by digital sampling and software calculation, which measuring may be done in either time-domain, or frequency-domain, using discrete Fourier transform or fast Fourier transform, and calculates the differential resistance if neither impedance is known, and the actual resistance of one impedance if the other is known;
wherein all such measurements derive from the energy absorption of the test substance.

6. A method for measuring conductivity or impedance, utilizing a sensor comprising:
at least one magnetic core, each core comprised of one or more pieces of a magnetic material, with each magnetic core describing a component of a circuit;
a primary coil wire wrapped around a section of the at least one magnetic core; and
at least one secondary coil wire wrapped around a section of the at least one magnetic core or at least one magnetic sensor affixed to the magnetic core or both, and:
connecting said primary coil to an electrical power source; and
electrically connecting a secondary coil or magnetic sensor to a measuring device, which measuring device measures an electrical signal present in such secondary coil or magnetic sensor with the aid of an amplifier and analog circuits, or by digital sampling and software calculation; or
in embodiments with a plurality of magnetic cores, and a plurality of secondary coils or magnetic sensors or both:
electrically connecting such secondary coils or magnetic sensors or both with:
a device which measures the differential signal of the secondary coils with the aid of a differential amplifier or by digital sampling and software calculation, which measuring may be done in either time-domain, or frequency-domain, using discrete Fourier transform or fast Fourier transform;
and at least partially immersing the sensor in or surrounding it with one or more test substances, and deriving the conductivity of the one or more test substances from the measurements thus obtained;
wherein all such measurements derive from the energy absorption of the test substance.

7. The method of claim 6, wherein the sensor comprises two magnetic cores in a single piece of magnetic material roughly describing a FIG. 8.

8. The method of claim 7, wherein each magnetic core has an additional coil wire wrapped around a section of it and connected to a potentiometer, and further comprising balancing the flux of the two magnetic cores with the potentiometers.

9. The method of claim 6, wherein the sensor comprises two magnetic cores wholly separate from each other, wherein the primary coil is wrapped around a section of each magnetic core.

10. The method of claim 7, wherein part of one magnetic core is immersed in a test substance.

11. The method of claim 10, wherein part of one magnetic core is immersed in a test substance, and part of the other magnetic core is immersed in another test substance.

12. The method of claim 7, wherein the test substance is ducted through a hose or pipe or similar conduit that is wrapped around a section of one of the magnetic cores.

13. The method of claim 7, wherein all of one magnetic core and part of the second are immersed in a test substance in a container, and differing conductance readings are correlated to differing test substance levels, and the test substance level is determined from the measurements obtained.

14. The method of claim 7, wherein the power source is AC;
wherein the sensor comprises an additional coil wire wrapped around a section of one magnetic core and connected to a first impedance, and yet another coil wire wrapped around a section of the other magnetic core and connected to a second impedance;
and further comprising having the device which measures the signal at the two ends of the secondary coils calculate the differential resistance if neither impedance is known, and the actual resistance of one impedance if the other is known.

* * * * *